(12) United States Patent
Nagarimadugu et al.

(10) Patent No.: US 7,994,328 B2
(45) Date of Patent: Aug. 9, 2011

(54) PROCESS FOR THE PREPARATION OF DONEPEZIL HYDROCHLORIDE

(75) Inventors: Mahesh Nagarimadugu, Hyderabad (IN); Arun Kumar Gupta, Hyderabad (IN); Ramesh Dandala, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 1218 days.

(21) Appl. No.: 11/703,948

(22) Filed: Feb. 8, 2007

(65) Prior Publication Data

US 2007/0191610 A1 Aug. 16, 2007

(30) Foreign Application Priority Data

Feb. 16, 2006 (IN) .............................. 255/CHE/2006

(51) Int. Cl.
   *C07D 211/32* (2006.01)
(52) U.S. Cl. ........................................ 546/206; 546/205
(58) Field of Classification Search .................. 546/205, 546/206
   See application file for complete search history.

(56) References Cited

U.S. PATENT DOCUMENTS

| 4,895,841 A | 1/1990 | Sugimoto et al. |
| 2007/0117846 A1 | 5/2007 | Imai et al. |
| 2009/0253746 A1 | 10/2009 | Soldevilla Madrid |

FOREIGN PATENT DOCUMENTS

| CA | 2616117 | * | 2/2007 |
| JP | 3992806 B2 | | 10/2007 |
| WO | WO 2007/013395 A1 | | 2/2007 |
| WO | WO 2007/108011 A2 | | 9/2007 |
| WO | WO 2008/010235 A2 | | 1/2008 |
| WO | WO 2008/126995 A1 | | 10/2008 |
| WO | WO 2009/084030 A2 | | 7/2009 |

OTHER PUBLICATIONS

Seddon "pseudopolymorph . . . " Crystal growth & design v.496) p. 1087 (2004) (two pages from internet).*
Braga et al. "Making crystals . . . " Roy. Sco. Chem. Chem Commun p. 3635-3645 (2005).*
Nagarimadugu et al. "Process for . . . " CA 147:277458 (2007).*
Endo et al. "intermediate for donepeizil . . . " CA13173566 (1997).*

* cited by examiner

*Primary Examiner* — Celia Chang
(74) *Attorney, Agent, or Firm* — Jay R Akhave

(57) ABSTRACT

The present invention relates to an improved process for the preparation of 1-benzyl-4-[(5,6-dimethoxy-1-indanon)-2-yl]methylpiperidine hydrochloride of Formula I.

5 Claims, No Drawings

Formula I

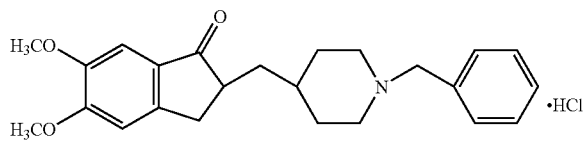

PROCESS FOR THE PREPARATION OF DONEPEZIL HYDROCHLORIDE

CROSS REFERENCE TO THE RELATED APPLICATION

This application claims the priority of Indian Application No. 255/CHE/2006, filed on Feb. 16, 2006.

FIELD OF THE INVENTION

The present invention relates to an improved process for the preparation of 1-benzyl-4-[(5,6-dimethoxy-1-indanon)-2-yl]methylpiperidine hydrochloride of Formula I, Formula I

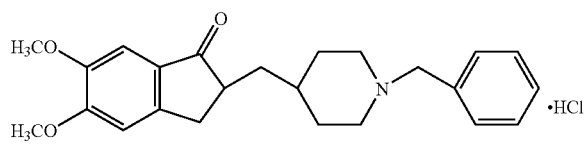

BACKGROUND OF THE INVENTION

1-Benzyl-4-[(5,6-dimethoxy-1-indanon)-2-yl]methylpiperidine hydrochloride, generically known as Donepezil hydrochloride, is used for the treatment of patients with various conditions involving memory loss, such as senile dementia of Alzheimer's type (DAT). Donepezil hydrochloride is marketed as oral tablets under the trade name of Aricept®.

Eisai Co., Ltd has disclosed Donepezil and its pharmaceutically acceptable salts in U.S. Pat. No. 4,895,841.

The process for the preparation of Donepezil described in this patent, involves the reaction of 5,6-dimethoxy-1-indanone (II) with 1-benzyl-4-piperidine-1-carboxaldehyde (III) in the presence of strong base such as lithium diisopropylamide under inert atmosphere followed by reduction of the resulting compound, i.e. 1-benzyl4-[5,6-dimethoxy-1-indanon)-2-ylidinyl]methyl piperidine (IV) to give the title compound of Formula (I) with an overall yield of 27.4% (Ref. Scheme 1).

Scheme-1

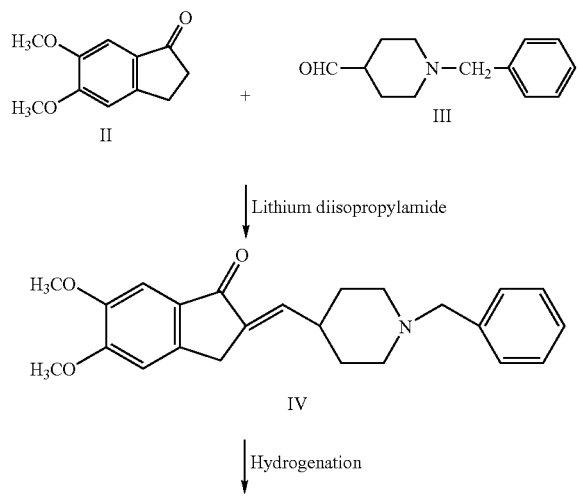

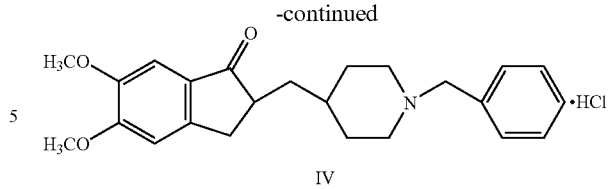

IV

The above process involves use of lithium diisopropylamide and cryogenic temperatures. Lithium diisopropylamide is expensive, toxic, pyrophoric in nature and easily decomposes with the moisture, Further, this process is low yielding and hence economically unattractive.

Japanese patent no. JP 11-171861 discloses a process for the preparation of 1-benzyl-4-[5,6-dimethoxy-1-indanon)-2-ylidinyl]methylpiperidine (IV) by condensation of 5,6-dimethoxy-1-indanone (II) with 1-benzyl-4-formylpiperidine (III) in presence of bases such as alkali metal alkoxide in a solvent selected from tetrahydrofuran.

This process also suffers from major disadvantages such as low yield and low purity of 1-benzyl-4-[5,6-dimethoxy-1-indanon)-2-ylidinyl]methylpiperidine (IV), a key intermediate in the preparation of Donepezil hydrochloride.

The reason for such low yield has not been described in any of the prior art. We have now found that the reason for the low yield is due to the formation of an undesired hydroxy compound of Formula V.

Formula V

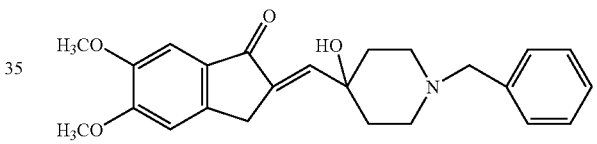

The compound (V) is formed up to the extent of 1%, because of the compound (IV) under going oxidation during the coupling reaction. This is further carried forward as an impurity in Donepezil Hydrochloride (I). Removal of this impurity in the final stage has often proved to be difficult and requires repeated crystallizations, which finally results in the low yield of compound of Formula I.

In the instant invention, it has been found that if the reaction of 5,6-dimethoxy-1-indanone (II) with 1-benzyl-4-formylpiperidine (III) in presence of alkali metal alkoxide is carried out in presence of a catalytic amount of antioxidants such as hydroquinone, butylated hydroxytoluene (BHT) etc., results in compound (IV) with high purity and reduces the formation of compound (V) to below detectable limits and can be used as such to produce Donepezil Hydrochloride of high purity.

OBJECTIVE OF INVENTION

The main objective of the present invention is to provide a simple and effective process for the preparation of Donepezil hydrochloride of high purity on commercial scale.

SUMMARY OF THE INVENTION

Accordingly, the present invention relates to an improved process for the preparation of 1-benzyl-4-[(5,6-dimethoxy-1-indanon)-2-yl]-methylpiperidine hydrochloride of Formula I.

Formula I

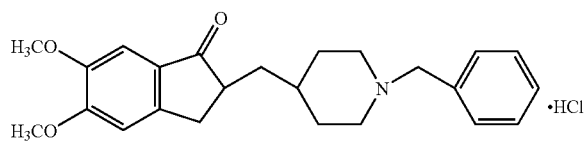

which comprises, (i) reacting 5,6-dimethoxy-1-indanone (II),

Formula II

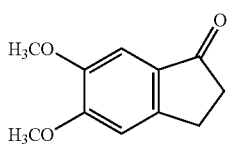

with 1-benzyl4-piperidinecarboxaldehyde (III)

Formula III

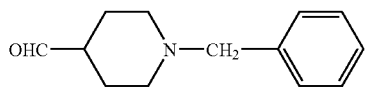

in presence of base and an antioxidant in a solvent to produce 1-benzyl-4-[5,6-dimethoxy-1-indanon)-2-ylidenyl]methyl] piperidine solvate (IV)

Formula IV

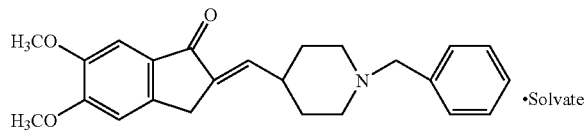

wherein solvate is selected from hydrocarbon such as toluene, (ii) reducing the compound (IV) with metal catalyst in a solvent or a mixture of solvents to produce 1-benzyl4-[(5, 6-dimethoxy-1-indanon)-2-yl]-methylpiperidine hydrochloride of Formula I, (iii) optionally treating aqueous solution of 1-benzyl-4-[(5,6-dimethoxy-1-indanon)-2-yl]methylpiperidine hydrochloride (I) containing 4-[5,6-dimethoxy-1-indanon)-2-yl]methylpiperidine (VI) as impurity in ≧0.4% by HPLC, Formula VI

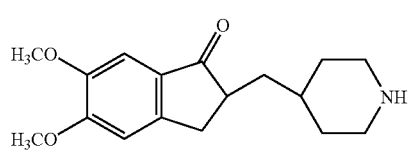

with benzyl halide in presence of base and phase transfer catalyst in a solvent to produce pure 1-benzyl-4-[(5,6-dimethoxy-1-indanon)-2-yl]-methylpiperidine hydrochloride (I).

DETAILED DESCRIPTION OF THE INVENTION 5,6-Dimethoxy-1-indanone (II) is reacted with 1-benzyl-4-piperidine-carboxaldehyde (III) in presence of a base selected from alkali metal alkoxide such as sodium methoxide, sodium ethoxide, potassium tert-butoxide and antioxidant selected from hydroquinone, butylated hydroxytoluene (BHT) etc. The reaction is carried out in an organic solvent selected from toluene, tetrahydrofuran, dimethoxyethane, dioxane, 1,4-dioxane, ethyl acetate, methyl acetate, alcohols such as ethanol, n-propanol, isopropanol, n-butanol, isobutanol, methoxyethanol etc., or mixtures thereof, at a temperature of 10-70° C. The base is added as such or mixed with a solvent selected from alcohols such as ethanol, n-propanol, isopropanol, n-butanol, isobutanol. The reaction is exothermic which is controlled by external cooling. After the completion of reaction, as ascertained by the known methods such as HPLC, water is added to the reaction mass and the pH of the reaction mass is adjusted to 7 to 9 most preferably 7.5 to 8.0 by adding acidic reagent selected from hydrochloric acid, sulfuric acid, trifluroacetic acid, acetic acid etc. During the above operation the temperature of the reaction is maintained between 0° C. to 20° C., but most preferably between 5° C. to 10° C. The product obtained is isolated by filtration and dried to give 1-benzyl-4-[5,6-dimethoxy-1-indanon)-2-ylidenyl]methyl]piperidine Toluene solvate (IV).

It has been observed that preparation of solvate of compound (IV) using above reaction conditions results in hydroxy impurity of compound (V) to less than 0.1% by HPLC analysis.

Hydrogenating the compound of formula IV is accomplished with a metal catalyst selected from raney nickel, ruthenium, rhodium or palladium metal of 5% or 10%, most preferably 5% palladium over carbon at a pressure of about 1 to 2 kg/cm$^2$. The hydrogenation is carried out in an organic solvent selected from tetrahydrofuran, ethyl acetate, methanol, ethanol, propanol, toluene or mixtures thereof, most preferable solvent is a mixture of tetrahydrofuran and toluene at a temperature of about 20° C. to about 60° C. most preferably at about 30° C. to 35° C. After the completion of the reaction, as ascertained by methods such as HPLC, the catalyst is filtered under nitrogen atmosphere and the residue is washed with solvent selected from above. The residue is converted to Donepezil hydrochloride without isolating Donepezil base formed.

In another embodiment of the present invention, if the aqueous layer of Donepezil hydrochloride contains debenzyl-donepezil of ≧0.4% by HPLC, analysis the reaction mass is treated with benzyl halide selected from benzyl bromide, benzyl chloride, benzyl iodide, most preferably benzyl bromide. Benzylation is carried out in a solvent selected from chlorinated hydrocarbon such as methylene chloride, chloroform, etc., in presence of a base selected from alkali metal carbonate such as potassium carbonate, sodium carbonate and phase transfer catalyst selected from tetrabutylammonium bromide, tetrabutylammonium fluoride, tetrabutylammonium iodide, tetramethylammonium iodide etc., at a temperature of 20° C. to 40° C., most preferably 20° C. to 25° C. for 1 to 3 hrs, most preferably 1 hr. After completion of the reaction the organic layer is separated and water is added followed by concentrated hydrochloric acid. The organic layer is separated and concentrated to get an oily residue contains Donepezil hydrochloride, which is recrystallised from solvents selected from alcohols, such as methanol, ethanol, propanol, isopropanol, butanol, etc., ethers such as diethyl ether, isopropyl ether, diisopropyl ether or mixtures thereof.

The following examples to prepare Donepezil Hydrochloride illustrate the nature of the invention and are provided for illustrative purpose only and should not be construed to limit the scope of the invention:

EXAMPLE

Step A

Preparation 1-benzyl-4-[(5,6-dimethoxy-1-indanon)-2-ylidenyl]Methylpiperidine Toluene Solvate (Dehydrodonepezil Toluene Solvate)

5,6-Dimethoxy-1-indanone (100 g, 0.52 mol) and hydroquinone (0.5 g) were suspended in toluene (500 ml) and heated to 55-60° C. under nitrogen atmosphere. 1-Benzyl-4-piperidinecarboxaldehyde (130 g, 0.64 mol) was added followed by methanolic sodium methoxide solution [prepared by dissolving sodium methoxide (57 g, 1.06 mol) in methanol (200 ml)] to the reaction mass at 55-60° C. After stirring at 66-70° C. for 30 minutes, the reaction mass was cooled to 5° C. and water (500 ml) was added. The pH of the reaction was adjusted to 7.8 with concentrated hydrochloric acid under cooling. The resulting product was filtered and washed with water (250 ml) followed by methanol (200 ml) to obtain dehydrodonepezil (203 g) as a toluene solvate with a HPLC purity of ≧99.5%.

[Toluene content: ~10% w/w as determined by its LOD on 1 g of sample at 105° C.]. $^1$H NMR (300 MHz, CDCl$_3$) 1.57-1.72 (m, 4H), 2.02-2.10 (m, 2H), 2.28-2.35 (m, 1H) 2.91-2.95 (brd, 2H), 3.53 (S, 2H), 3.59 (S, 2H), 3.93 (S, 3H), 3.98 (S, 3H) 6.66 (dt, 1H, 9.6 Hz, 1.92 Hz), 6.90 (S, 1H), 7.29 (S, 1H), 7.13-7.34 (m, 5H) [Signals due to toluene are observed at 2.35 (S), 7.17 (m) and 7.25 (m)]

Step B

Preparation of 1-benzyl-4-[(5,6-dimethoxy-1-indanon)-2-yl]-methylpiperidine Hydrochloride [Donepezil Hydrochloride]

1-Benzyl-4-[(5,6-dimethoxy-1-indanon)-2-ylidenyl]methylpiperidine toluene solvate (125 g 0.33 mol) was dissolved in a mixture of toluene (3563 ml) and tetrahydrofuran (187 ml) and heated to 55-60° C. The reaction mass was hydrogenated with 5% palladium on charcoal (6.25 g, 50% w/w moisture) with hydrogen pressure of 30-35 PSI at 30-35° C. for two hrs. The catalyst was filtered off and water (1250 ml) was added followed by concentrated hydrochloric acid (52 g) at 25-30° C. Aqueous layer containing 1% debenzyldonepezil by Qualitative HPLC analysis was treated with benzyl bromide (0.75 g) in presence of tetrabutylammonium bromide (0.63 g) and potassium carbonate (1.5 g) after basification of aqueous layer with ammonia in order to convert debenzyldonepezil to Donepezil. Aqueous layer was extracted with methylene chloride (750 ml) and organic layer was treated with concentrated hydrochloric acid (52 g). Organic layer was concentrated under reduced pressure and resulting residue was treated with methanol (375 ml) and diisopropyl ether (188 ml) to crystallize Donepezil Hydrochloride Form-1 (106.5 g) with HPLC purity of ≧99.7%.

We claim:
1. An improved process for the preparation of 1-benzyl-4-[(5,6-dimethoxy-1-indanon)-2-yl]methylpiperidine hydrochloride of Formula I

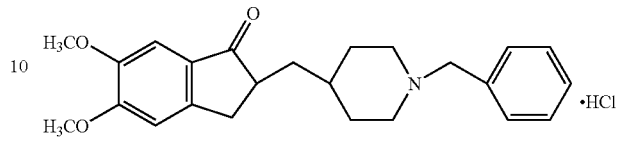

Formula I which comprises,
(i) reacting 5,6-dimethoxy-1-indanone (II),

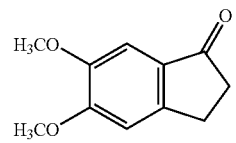

Formula II with 1-benzyl-4-piperidinecarboxaldehyde (III),

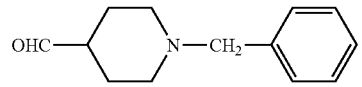

Formula III in presence of base and an antioxidant to produce 1-benzyl-4-[5,6-dimethoxy-1-indanon)-2-ylidenyl]methyl]piperidine toluene solvate,

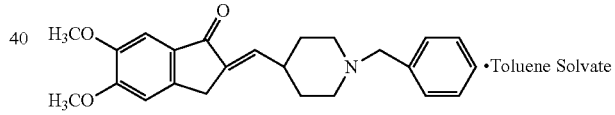

(ii) hydrogenating 1-benzyl-4-[5,6-dimethoxy-1-indanon)-2-ylidenyl]methyl]piperidine toluene solvate with a metal catalyst in a solvent or mixture of solvents followed by treating the resulting compound with hydrochloric acid to produce 1-benzyl-4-[(5,6-dimethoxy-1-indanon)-2-yl]methylpiperidine hydrochloride of Formula I.

2. A process according to claim 1, wherein the base used in step (i) is selected from alkali metal alkoxide such as sodium methoxide, sodium ethoxide, potassium tert-butoxide.

3. A process according to claim 1, wherein the anti-oxidant used in step (i) is selected from hydroquinone or butylated hydroxytoluene (BHT).

4. A process according to claim 1, wherein the reduction step is carried out in a solvent selected from tetrahydrofuran, ethyl acetate, methanol, ethanol, propanol, toluene or mixtures thereof.

5. A process according to claim 4, wherein said solvent is a mixture of tetrahydrofuran and toluene.

* * * * *